United States Patent
Pugach et al.

(10) Patent No.: US 7,309,125 B2
(45) Date of Patent: Dec. 18, 2007

(54) METHOD AND APPARATUS FOR DETECTING ABNORMALITIES IN SPATIAL PERCEPTION

(76) Inventors: Vladimir Pugach, 17-83 Lenina Street, Izevsk, 426076 (RU); Svetlana Tikhonova, 1940 Mount Vernon, Mountain View, CA (US) 94040; Vitali Tikhonov, 1940 Mount Vernon, Mountain View, CA (US) 94040

( * ) Notice: Subject to any disclaimer, the term of this patent is extended or adjusted under 35 U.S.C. 154(b) by 307 days.

(21) Appl. No.: 11/147,706

(22) Filed: Jun. 9, 2005

(65) Prior Publication Data
US 2007/0013868 A1  Jan. 18, 2007

(51) Int. Cl.
*A61B 3/08* (2006.01)

(52) U.S. Cl. ...................... 351/201; 351/209
(58) Field of Classification Search ........... 351/201, 351/209–211
See application file for complete search history.

(56) References Cited

U.S. PATENT DOCUMENTS

| | | |
|---|---|---|
| 4,838,676 A * | 6/1989 | Buget et al. ............... 351/202 |
| 4,973,149 A | 11/1990 | Hutchinson |
| 5,422,690 A | 6/1995 | Rothberg et al. |
| 5,555,895 A | 9/1996 | Ulmer et al. |
| 5,668,622 A | 9/1997 | Charbonnier |
| 5,689,325 A | 11/1997 | Isogai et al. |
| 6,334,683 B2 | 1/2002 | Apple et al. |
| 6,517,204 B1 * | 2/2003 | Ghahramani ............... 351/201 |
| 2006/0087618 A1 * | 4/2006 | Smart et al. ............... 351/222 |
| 2007/0146630 A1 * | 6/2007 | Divo ......................... 351/200 |

* cited by examiner

*Primary Examiner*—Jordan M. Schwartz (57) ABSTRACT

An apparatus for detecting abnormalities in spatial perception that consists of a first transparent screen in a close-vision field and a second screen seen through the first one and located in a far-vision field of a person being tested. The apparatus is provided with devices for forming images selectively on the first or second screen and with a device for tracking trajectories of the eye pupils while following the images. The method is based on detecting specific irregularities in trajectories of the eye pupils, such as nystagmuses, cut-offs, sudden drops of the gaze, etc., when a person follows the smooth trajectory of a moving image on a selected screen, or when the size and position of the eye pupil change with certain irregularity in response to instantaneous switching of images between the screens without changing the position of the person's head.

20 Claims, 5 Drawing Sheets

METHOD AND APPARATUS FOR DETECTING ABNORMALITIES IN SPATIAL PERCEPTION

FIELD OF THE INVENTION

The present invention relates to the field of neuropsycology, psychophysiology and neurophysics of the brain, and more specifically, to a method and apparatus for detecting abnormalities in spatial perception that may be caused, e.g., by brain disorder or damage, stress, tiredness, psychological traumas, etc.

BACKGROUND OF THE INVENTION

It is known that some brain abnormalities, disorders, or damage may cause abnormalities of spatial perception and attention disorders that in some professions may lead to increase in errors to the extent that the individual becomes unsuitable for the profession. Examples of such professions that may require extraordinary attention are pilots, air-traffic controllers, vehicle drivers, etc. The problems associated with abnormalities in spatial perception concern not only people involved in professions where lack of attention may lead to high-risk situations and even to fatal consequences, but also to events of the everyday life such as studying, operation on machine tools, computer programming, management, etc. In view of the above, it is important in some fields of human activities to test the individuals for fitness to their professions or types of work they conduct.

The method and apparatus of the invention are also important tools for testing children, e.g., with Attention Deficit Hyperactivity Disorder (ADHD).

Heretofore, many methods and apparatuses are known in the art for testing spatial perception skills and thus for detecting fitness to the profession or activity.

For example, U.S. Pat. No. 4,973,149 issued in 1990 to T. Hutchinson discloses a system for eye movement detection that utilizes an infrared light emitting diode mounted coaxially in front of the lens of an infrared sensitive video camera for remotely making images of the eye of a computer operator. The reflected light causes bright eye effect which outlines the pupil as brighter than the rest of the eye and also causes an even brighter small glint from the surface of the cornea. The computer includes graphic processing which takes a video image, digitizes it into a matrix of pixels and analyzes the matrix. Using special algorithms, the analysis determines the location of the pupil's center and the location of the glint relative to each other and with this information determines where the eye is gazing. If the eye-gaze is for a predetermined time at images in selected areas on the computer screen, the area is selected and results in actuation of other devices or the presentation of additional images on the screen.

U.S. Pat. No. 5,555,895 issued in 1996 to E. Ulmer, etc. describes a process and a device for analyzing the movement of the eye or eyes of a patient, i.e., of a human being or animal. A device comprising a first video camera, a second video camera, which first and second cameras are mounted on a spectacle frame and are rigidly connected together and form part of a removable module; said first and second cameras have points of sight of their respective scenes which are close. The technical domain of the invention is that of the manufacture of devices for measuring the movement of the eyes.

U.S. Pat. No. 5,422,690 issued in 1995 to M. Rothberg, et al. describes a fitness impairment tester that implements a self-administered screening test to determine whether a subject is physically impaired. The tester is fully automated to respond to the entering of a subject's personal identification on a keypad. By superposing two different colored lights as viewed through an eyepiece, the subject aligns his or her pupil on the optical axis of pupil imaging optics which focuses an image of the subject's pupil on an image plane. The tester automatically recognizes this condition and audibly signals the subject that the test is about to begin. Light stimuli are provided to cause the pupil to change size and the eye to move. Pupil diameter measurements are made of the image of the subject's pupil in response to on axis light stimuli. Eye tracking of the subject's eye in response to moving light stimuli provide a measure of eye movements. The data acquired by measuring pupil diameter and saccadic movements of the subject's eye as a function of time are compared with baseline data for the subject stored in a database, and an output indicative of a deviation of said current measurements from said baseline data is provided.

U.S. Pat. No. 5,668,622 issued in 1997 to C. Charbonnier describes a device for measuring the position of the fixing point (P') of an eye on a video screen comprising: a mobile support positioned close to the eye and on which first illumination means and a video camera are fixed so as to embody images of the eye, and a fixed support distant from the eye and on which the video screen orientated opposite the eye and a plurality of luminous sources illuminating the eye in alternative with the first illumination means are positioned and disposed around the video screen so as to create on the eye corneal reflections and means for treating the images obtained from the eye. The invention also concerns an eye illumination method in which the eye is illuminated by flashes each emitted at the end of each taking of images, as well as an application of the device for displaying on the video screen images which change according to the movements of the eye wherein a high resolution zone (Z) is defined around the fixing point (P') and for moving this zone according to the movements of the eye.

However, none of the references mentioned above and known to the inventors discloses a universal method or apparatus that provide testing of an individual with regard to abnormalities in spatial perception with the use of a two-screen principle for detecting specific deviations from normal perception of objects, stationary or moving, in the close-vision field and the far-vision field. Furthermore, none of the references mentioned above allows complete analysis of static and dynamic phenomena that occur in the spatial perception in switching the gaze on an object from the close-view field to the far-view field, or vice versa.

SUMMARY OF THE INVENTION

It is an object of the invention to provide a universal method and apparatus for testing individuals with regard to abnormalities in spatial perception with the use of two screens installed in the close-vision field and the far-vision field by observing the patterns of the eye pupil movements in tracking the objects stationary or moving in the close screen, far screen, in both screens, and in switching from one screen to another. It is another object to provide the aforementioned method and apparatus that can detect abnormalities in spatial perception undetectable by other known methods and apparatuses. Still another object is to provide a method and apparatus for determining professional fitness of an individual to a specific profession, especially for professions associated with high risks. A further object is to provide testing of the individuals with regard to spatial perception on the basis of personalized data bases accumulated for specific activities and for specified individuals.

According to the method of the invention, a patient to be tested is sat in a chair and his/her head is fixed against movements so that only the eyes can follow the object. The object may comprise a moving light signal of any configuration and sufficient intensity of brightness. The light signal is first projected onto a close screen located in the area of the aforementioned close field. When the viewer's eye pupils follow the moving light signals, movements of the eye pupils are registered, e.g., by means of an image sensor. Such registrations are carried out separately for the observations in the close and far fields. If necessary, without changing positions of the viewer's head and without interrupting the eye movement registration, a projection of the light signal is switched to the far screen located in the aforementioned far field. Movements of each eye and changes in the size of the pupils are registered individually and the results of the registration can be recorded in a computer and later compared for both eyes, as well as with the previously accumulated data for detecting the dynamics of changes in the viewer's spatial perception. Light signal trajectories may be different and may be distinguished for diagnosing different spatial perception disorders or for other purposes. More specifically, the patterns of normal perception are compared with the patterns of abnormal perception, and the comparison will distinctly reveal the presence or development of the disorder.

The above method is realized with the use of an apparatus of the invention that comprises: means for fixation of the viewer's head; a transparent close screen located at the close field distance from the alleged position of the viewer's eyes so that a horizontal axis passes from the eyes substantially through the center of the close screen; a far screen that may be transparent or opaque located at the far field distance from the alleged position of the viewer's eyes and being substantially aligned with the close screen; an image sensor for registering positions of the viewer's eye pupils; means for creating an image on the close screen; means for creating an image on the far screen; a data acquisition and processing system; and data indication or display unit. The position of the head fixation means can be adjustable, and the screens may have special profiles, e.g., parabolic, spherical, or the like.

BRIEF DESCRIPTION OF THE DRAWINGS

FIG. 5a illustrates a test with linear movements of the light spot in direct and reverse directions; FIG. 5b illustrates an abnormality revealed in sudden jump of the gaze in the downward or upward direction; FIG. 5c shows a curvilinear trajectory of the pupil in following linear movements of the light spot; and FIG. 5d shows a nystagmus that may occur in the test of FIG. 5a.

DETAILED DESCRIPTION OF THE INVENTION

The invention is based on the common knowledge in the field of human physiology and on the inventors' observations that in the visual perception each individual uses the close-vision field and the far-vision field that exist irrespective of our consciousness. For example, when an individual is reading a book or looking at a computer keyboard, he/she uses the close-vision field. The inventors have found that in an adult person on average the close-vision field is located at a distance of up to 30-60 cm from the observer's eye, and the center of the close-vision field is generally below the horizontal plane passing through the viewer's eye pupil, e.g., 15° below the aforementioned horizontal plane. The far-vision field is extended from the close-vision field to infinity, e.g., from 40-60 cm to infinity. Examples of the far-vision field are situations on the road during driving, a blackboard in a class-room, a football field, the control panel of an air-traffic controller, the control panel of an operator of a nuclear power station, etc. A viewer cannot simultaneously see objects distinctly in both fields, and in switching from one field to another the viewer changes the so-called plane of accommodation and angle of observation.

The phenomenon of visual perception of objects located in the close-vision field (hereinafter referred to as "close field") and in the far-vision field (hereinafter "far field") are different and have a complicated psychophysiological nature. With regard to the psychophysiological processes that occur in viewing objects, all individuals can be roughly divided into the following four categories: 1) people who have normal spatial perception in the close field and far field; 2) people who have normal spatial perception in the close field but abnormal perception in the far field; 3) people who have abnormal spatial perception in the close field but normal perception in the far field; and 4) people who have abnormal spatial perception in the close field and abnormal perception in the far field.

The aforementioned abnormalities can be revealed in specific movements of the viewer's eye pupils, e.g., in the horizontal, vertical, or orbital movements of the eye pupils. This is true for observing the objects in both the close field and the far field. In the medicine such movements of the eye pupils are known as saccadic nystagmatic movements, and in the neurophysics such movements of the eye pupils are known as saccadic nystagmus.

Saccades are used to bring the eye rapidly from one point of regard to another. As one does not see during a saccade, it is best to get them over as quickly as possible. Accordingly, saccades typically move at speeds between 200 and 600 degrees/sec; to move gaze 90 degrees, it takes ⅓ second (which still seems like a rather long time not to see). Things that happen very quickly often have a tendency to get out of control. With saccades, most disorders consist of either instability (oscillation, flutter and opsoclonus), or inability to inhibit saccades (square wave jerks, saccadic intrusions). Methods of recording saccadic nistagmuses are known and described, e.g., by Timothy C. Ham in articles "Saccadic Nystagmus"

The inventors herein have found one more specific abnormality that may occur in spatial perception in some individuals. The inventors called this abnormality a "phenomenon of a broken mirror". This phenomenon is revealed as a discontinuity of vision in the peripheral areas of the aforementioned fields, especially in rapid switching from one field of vision to another. The present invention is based on the fact that the pattern of the eye pupil movements is related to disorders in the spatial perception. Another abnormality found by the inventors in the close-vision or far-vision field is the so-called "sudden slide of the gaze in the upward or downward direction".

According to the method of the invention, a patient to be tested is sat in a chair and his/her head is fixed against movements so that only the eyes can follow the object. The object may comprise a moving light signal of any configuration and sufficient intensity of brightness. The light signal is first projected onto a close screen located in the area of the aforementioned close field. When the viewer's eye pupils follow the moving light signals, movements of the eye pupils are registered, e.g., by means of an image sensor. Such registrations are carried out separately for the observations in the close and far fields. If necessary, without changing positions of the viewer's head and without interrupting the eye movement registration, projection of the light signal is switched to the far screen located in the aforementioned far field. Movements of each eye and changes in the size of the pupils are registered individually and the results of the registration can be recorded in a computer and later compared for both eyes, as well as with the previously accumulated data for detecting the dynamics of changes in the viewer's spatial perception. Light signal trajectories may be different and may be distinguished for diagnosing different spatial perception disorders or for other purposes. More specifically, the patterns of the normal perception are compared with the patterns of abnormal perception and the comparison will distinctly reveal the presence or development of the disorder.

The above method is realized with the use of an apparatus of the invention that comprises: means for fixation of the viewer's head; a transparent close screen located at the close field distance from the alleged position of the viewer's eyes so that a horizontal axis passes from the eyes substantially through the center of the close screen; a far screen that may be transparent or opaque located at the far field distance from the alleged position of the viewer's eyes and being substantially aligned with the close screen; an image sensor for registering positions of the viewer's eye pupils; means for creating an image on the close screen; means for creating an image on the far screen; a data acquisition and processing system; and data indication or display unit. The position of the head fixation means can be adjustable, and the screens may have special profiles, e.g., parabolic, spherical, or the like.

Figure 1:
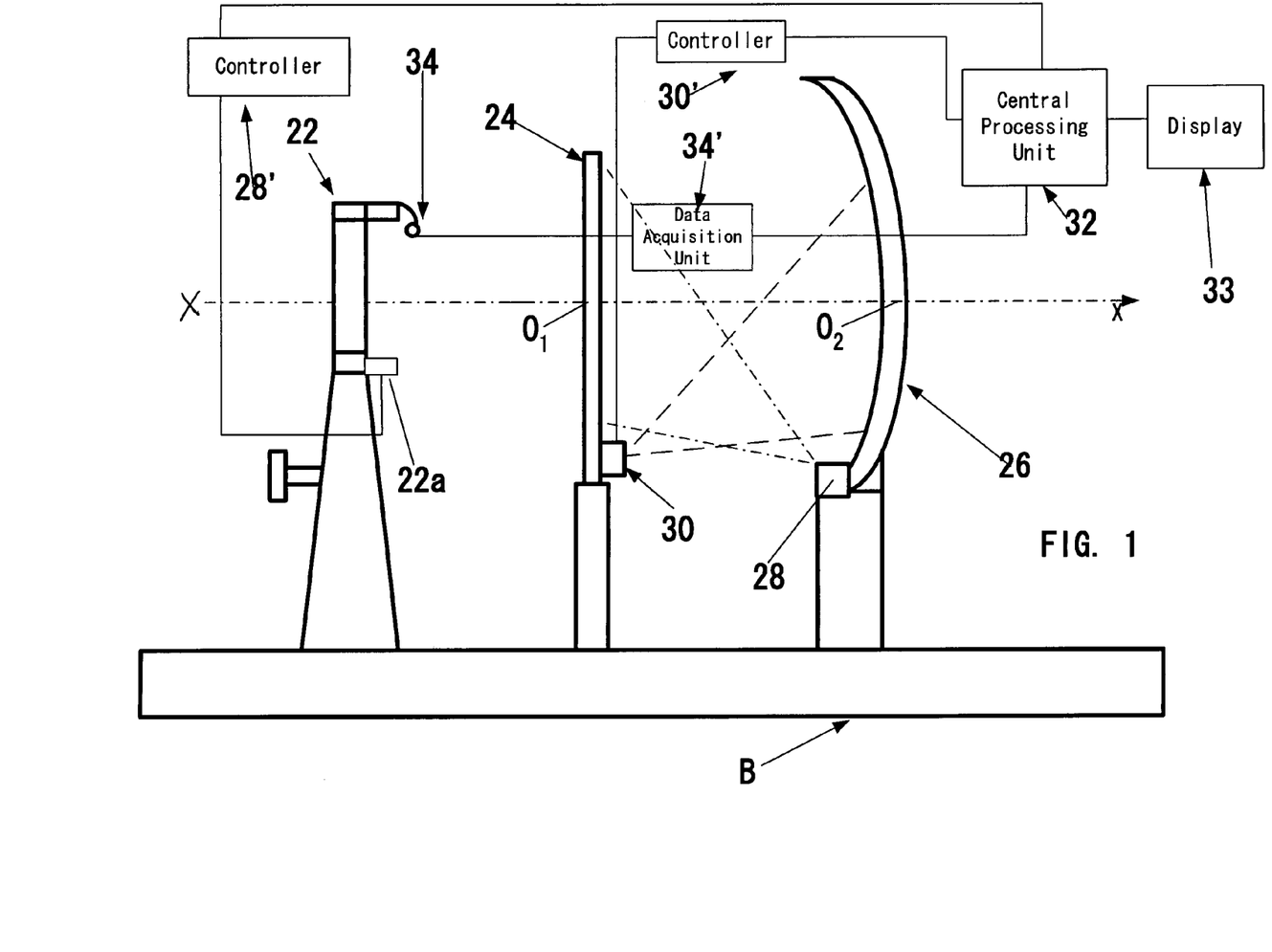
FIG. 1 is a schematic side view of the apparatus of the invention.

A general side view of the apparatus of the invention is shown in FIG. 1. The apparatus, that in general is designated by reference numeral 20, consists of a base support B, a head fixation device 22 secured to the base support B for fixation of the patient's head during testing, a transparent close screen 24 supported by the base support B and installed at the close-field distance from the patient's eyes, a curvilinear transparent or opaque far screen 26 supported by the base support B and located at a far-field distance from the patient's eyes and aligned with the position of the close screen 24 in the sense that the horizontal axis X-X passes through the point in the middle between the eyes and through the geometrical centers $O_1$ and $O_2$ of the close screen 24 and the far screen 26, respectively. The concave side of the curvilinear far screen 26 faces the patient (not shown). The apparatus is further provided with an image generating unit 28 for projecting a moving image onto the close screen 24 that may be located in any position convenient for projecting a moving image, e.g., a moving light spot, onto the close screen 24. In the embodiment of FIG. 1 the image generating unit 28 is shown in a position between the close screen 24 and far screen 26. A second image generating unit 30 is intended for projecting a moving image onto the far screen 26. This unit also may be positioned in any location convenient for obtaining a relatively undistorted moving image, e.g., a light spot, on the far screen 26. In the embodiment shown in FIG. 1, the image generating unit 30 is positioned near the edge of the close screen 24. Furthermore, the image generating units 28 and 30 should be located in positions that exclude direct exposure of viewer's eyes to the laser beams that generate the images. Moreover, the intensity of the light reflected and scattered from the images created on the screens and perceived by the viewer's eyes should be within the limits specified by appropriate standards and safety codes, e.g., standards of NBS USA.

The image generating units 28 and 30 are provided with controllers 28' and 30', respectively, for controlling their operation under commands of a central processing unit (CPU) 32 that is connected to both controllers.

The apparatus is equipped with image sensors for continuous tracking movements and recording images of the eye pupils. Since the sensors for tracking movements of the eye pupils are identical for both eyes, only one of them, i.e., the image sensor 34 is shown. The image sensor or eye tracking device 34 should be positioned in a location that provides unobstructed view of the patient's eyes. The eye tracking device 34 is connected to the CPU 32 via a data acquisition unit 34' that received the data from the image sensor and transmits it to the CPU for further processing.

Having described the apparatus 20 of the invention in general, let us consider now some details of separate units.

The head support 22 is a unit, on which the head of a patient (not shown) is to rest. This can be a device conventionally used in any ophthalmologic apparatus, e.g., of the type described in U.S. Pat. No. 5,689,325 issued in 1997 to N. Isogai, et al. As usual, the head support is provided with mechanisms for adjusting the position of the head support, and, hence of the patient's eyes, so as to align the axis X-X (FIGS. 1 and 2) with respect to the centers $O_1$ and $O_2$ of the screens 24 and 26.

The eye pupil position data obtained by the eye tracking device 34 is used to detect eye motion during the test. Such a device is disclosed, e.g., in U.S. Pat. No. 6,334,683 issued in 2002 to H. Apple, et al. Conventional video based eye tracking systems automatically recognize and track the position of eye positions based on landmarks present within an image of a human eye. Such equipment requires illumination of the eye, e.g., by infrared (IR) light. IR light typically 850 to 930 nanometers (nm) is used because it provides a good picture contrast between the pupil and iris. Additionally, the use of IR light decouples the lighting source from other visual sources which do not contain the infrared wavelengths.

The eye, illuminated by invisible IR light, e.g., from an IR light source 22a, is imaged by the eye tracking device 34, e.g., in the form of an infrared sensitive video camera. Under normal conditions, the pupil of the eye appears as a dark hole to the illumination. The dark pupil image is input to the CPU 32 via the data acquisition and processing unit 34' that outputs pupil size and position coordinates relative to the scan of the camera. The CPU 32 is connected to a display unit 33 that can visually display the results of the test.

An example of the eye illumination device and position thereof with respect to the patient's eye on the head support is shown, e.g., in U.S. Pat. No. 5,668,622 issued in 1997 to C. Charbonnier, et al.

The transparent close screen 24 can be made from a transparent material of high light transmissivity, e.g., no less than about 99.0%. The close screen may be flat or slightly negatively curved (e.g., with the radius of 30 to 60 cm) with respect to the moving image generating unit 28 and can be made from glass or plastic and may have a coating capable of partially absorbing and scattering the light of a predetermined wavelength, e.g., 632.8 nm, or 532 nm, i.e., of the light emitted by the image projecting device. It should provide clear view of the images on the far screen from the position of the patient eyes when his/her head is fixed on the head support 22 for testing.

The far screen 26 may be transparent or opaque and can be made from glass, plastic, or other materials. For example, it can be made from an opaque glass. The opaque material is preferable. The far screen may be colored in order to ensure distinct and contrast view of the moving image. The far screen may have a coating that ensures partial absorption and scattering of the incident light. The far screen has a curvilinear profile shown in FIG. 1. It may be spherical, paraboloid of revolution, or may have any other suitable profile.

The average radius of curvature may be of about 80 cm to 150 cm. These numbers should not be construed as limiting the scope of the invention and are given only as an example.

The moving image generating units 28 and 30 may comprise laser light sources or light beam deflectors that may emit light beams that in a static state produce on the respective screens light spots having a diameter of 2 to 5 mm. Movements of the light beams are controlled by means of so-called electro-optical image generator or laser image generators with moving heads that control positioning of the light spot within a wide range of movement speeds and with possibility of coordinating positions of the light beam spots. Such laser light sources are commercially produced, e.g., by International Laser Production. The above-mentioned light sources may produce light spots moving from minimal speeds to high speeds undetectable by a human eye. For the purposes of the invention, the most optimal speed for moving the light spot on the close screen 24 and on the far screen 26 should be within the range of 1 cm/sec to 100 cm/sec.

Some basic testing procedures with the use of the method and apparatus of the invention shown and described with reference to FIGS. 1 and 2 will now be described with reference to FIGS. 2-6.

Figure 2:
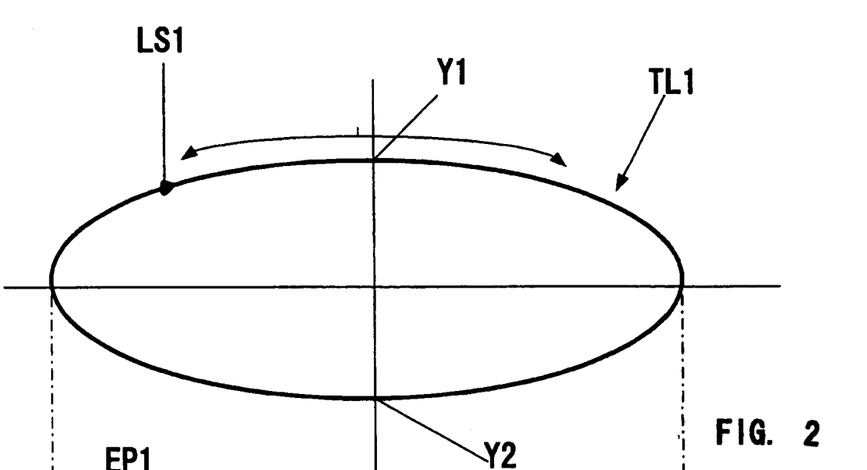
FIG. 2 is a view illustrating an oval trajectory of a light spot on the screen and an associated trajectory of the eye pupil.

The test of spatial perception shown in FIG. 2 can be carried out by projecting a moving object, e.g., a light spot on the close screen 24 or far screen 26 (FIG. 1) from the moving image generating units 28 and 30. The upper part of FIG. 2 shows the pattern of movement of a light spot LS1 that moves along a selected trajectory, e.g., substantially oval trajectory shown by an arrowed line TL1. The lower part of FIG. 2 shows the trajectory EP1 of the of the patient's eye pupils registered when the patient's eyes followed the light spot LS1. In the case of normal perception, the trajectory should be similar to the trajectory TL1, i.e., free of nystagmatic movements.

The test is started from a predetermined position of the light spot LS1, e.g., from point Y1. The light spot LS1 moves in a clockwise direction with a predetermined speed, first from point Y1 to point Y2 (FIG. 2). The light spot LS1 is then discontinued for a time sufficient for the eye to accommodate for the next observation (approximately, no less than 0.8 to 1.2 sec.). If necessary, the patient may be asked if he/she is ready for the next step of the test. The movement of the light spot LS1 is then resumed from the same point Y1 to the point Y2, but in the counterclockwise direction. In both movements, the pattern of the eye pupil movements are tracked and recorded by means of the eye movement tracking device 34 (FIG. 1). The recorded data is transmitted to the CPU 32 and, if necessary, displayed on the display unit 33.

Figure 3:
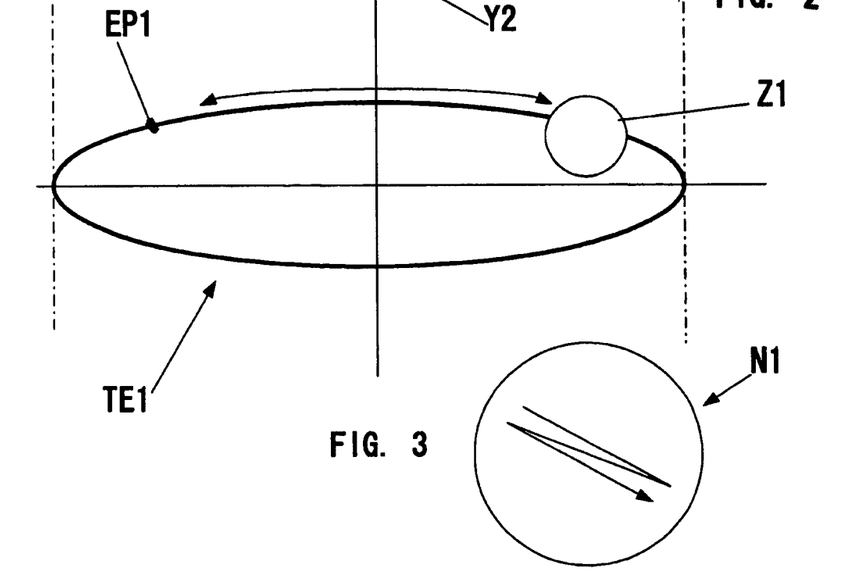
FIG. 3 shows a nystagmus that may occur as an abnormality of spatial perception in the test of FIG. 2.

In the case of a normal spatial perception, the trajectory TE1 of the eye pupil movements will be free of any nystagmuses on any part of the trajectory TE1. FIG. 3 shows on a larger scale a nystagmus N1 that occurred in the zone Z1 of FIG. 2. Although the nystagmus may comprise reciprocal movements of the eye pupil along the same line, for simplicity of explanation the nystagmatic movements are shown as a zigzag line. The nystagmus means that at a certain period of time the patient does not see the light spot LS1 and therefore may be evaluated as a person having spatial perception deficit.

Figure 4:
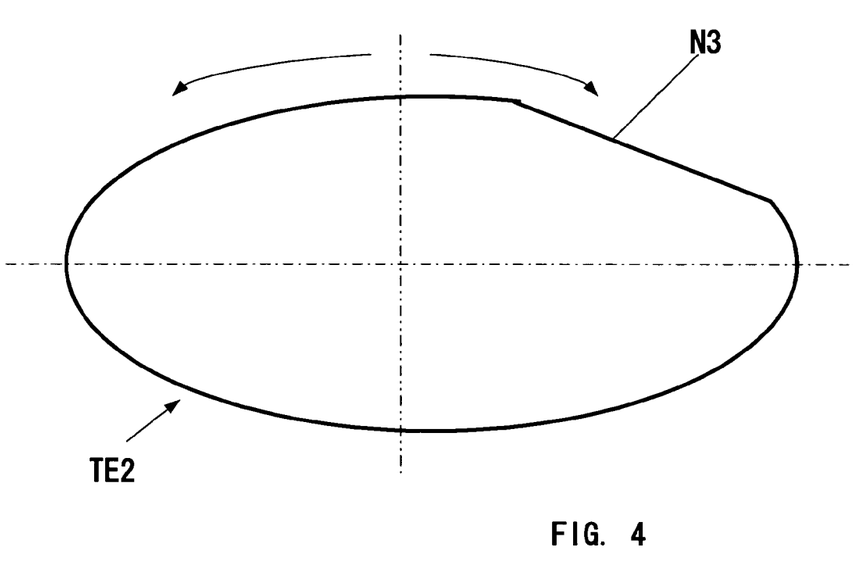
FIG. 4 shows another abnormality of spatial perception in the test of FIG. 2 that is revealed as a chordal cut-off in the oval trajectory of the pupil movement.

Another example of the same test as in FIG. 2 may detect another defect of the spatial perception that is shown in FIG. 4. In the case of spatial perception deficit the patient may develop a cut-off in following a smooth trajectory of the type as TL1 (FIG. 2). This cut-off is shown in FIG. 4 as a chordal line N3. The cut-off may occur on any part of the trajectory TE2 of the pupil.

Figure 5:
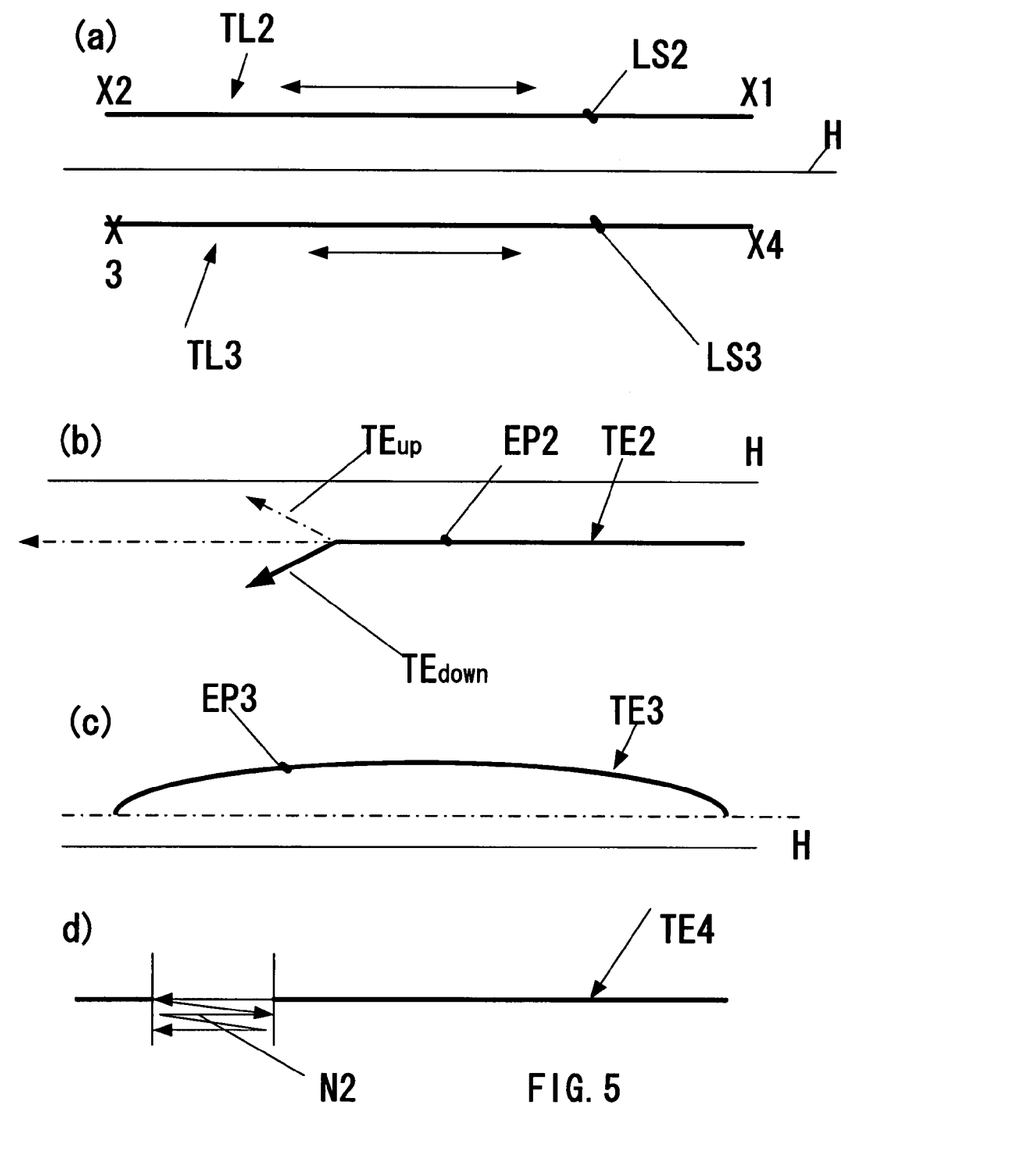

FIGS. 5(*a-d*) illustrate the test which is similar to the one shown in FIG. 2 but with linear reciprocal movements of the light spot. Line H designates a horizontal plane that contains line X-X shown in FIG. 1, i.e., the line that passes through the middle point between the eyes and the centers of the screens 24 and 26. In that case, in FIG. 5*a*, the line X1-X2 will depict the trajectory TL2 of the light spot LS2 on the far screen 26, and the line X3-X4 will depict the trajectory TL3 of the light spot LS3 on the close screen 24. It can be seen that the horizontal plane designated by line H is located between the trajectories TL2 and TL3.

In the test, the light spot TL2 starts its movements, e.g., from a point X1 in the forward direction (from right to the left in FIG. 5*a*) and then in a reverse direction from a point X2 (i.e., from left to the right).

In FIG. 5*b*, line TE2 designates the trajectory of movement of the eye pupil EP2 in following the movement of the light spot LS3 on the close screen 24 (FIG. 1). A defect that can occur in this test is normally revealed as a sudden drop of the gaze in the downward direction ($TE_{down}$) or in the upward direction ($TE_{up}$) (FIG. 5*b*). The inventors have noticed that this phenomenon occurs predominantly in testing movements only in the close-vision field. The normal spatial perception will correspond to a straight-line trajectory in both fields, i.e., without any sudden drops.

In FIG. 5*c*, the curved trajectory TE3 shows another abnormality that, in response to the linear movement of the light spot LS2 (FIG. 5*a*) in the forward and reverse direction, is reveled as curvilinear movement of the eye pupil EP3.

FIG. 5*d* illustrates another abnormality in the spatial perception, which is similar to the one shown in FIG. 3 but consists of linear nystagmus shown in the form of zigzag line N2. In fact, the zigzag line is shown conventionally as the movement may comprise reciprocations along the same line. There may be more than one nystagmus on the same trajectory TE4 shown in FIG. 5*d*.

Figure 6:
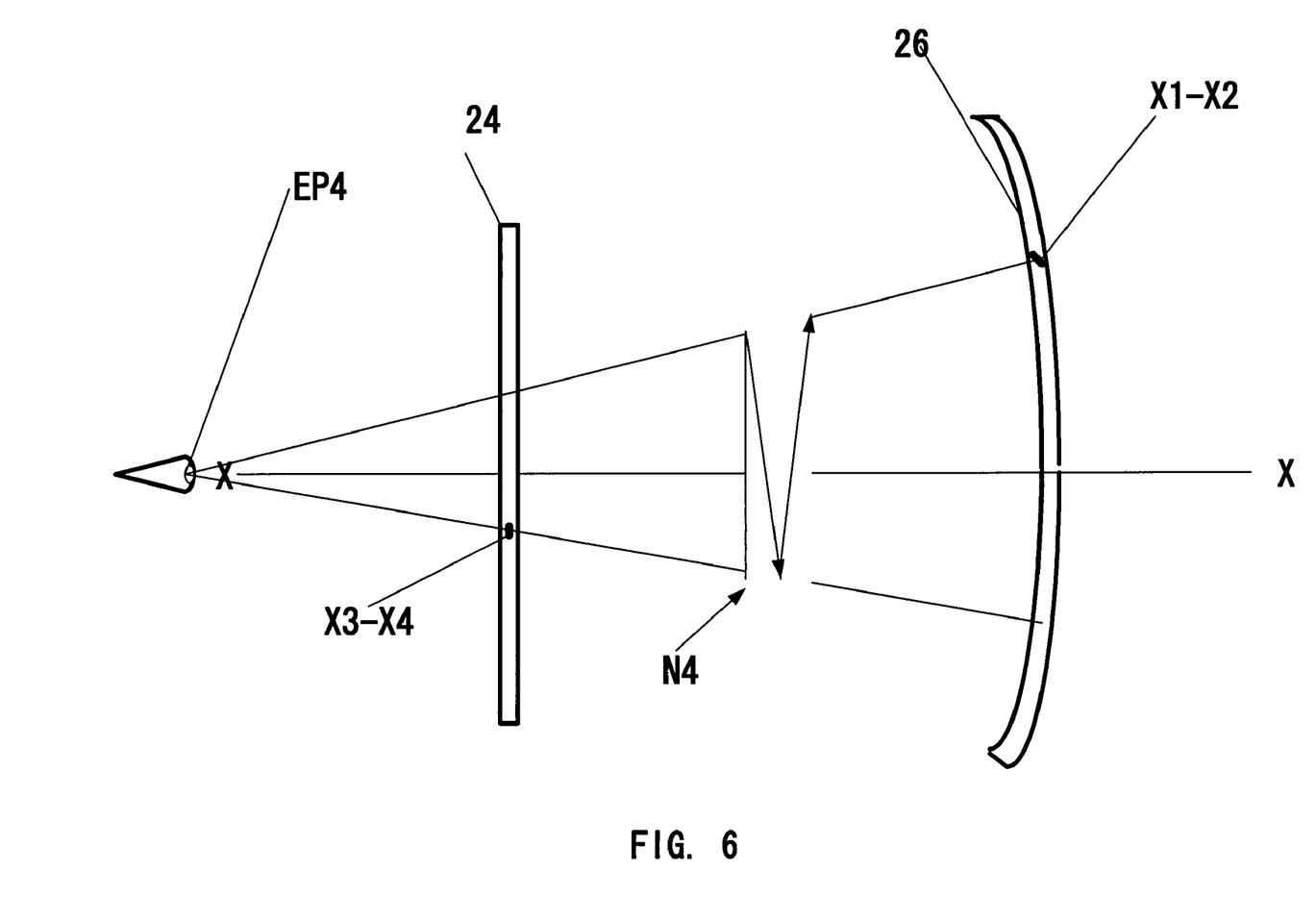
FIG. 6 is a schematic view of a test performed by instantaneous switching of the image between the screens.

FIG. 6 shows the spatial perception test that reveals abnormalities in switching the gaze from the close-vision field to the far-vision field and vice versa. This test is fulfilled by instantaneously switching the image from one screen to the other. This is applicable to any tests described above with reference to FIGS. 2 to 5, but without changing the position of the patient's head. The light spot may be moveable or stationary but the switch should instantaneous. The reaction is measured by tracking and recording the time and the movements of the eye pupil EP4 (FIG. 6) in following the light spot. If necessary, the reaction may be controlled by recording and measuring changes in the positions and diameter of the eye pupil. Methods of measuring the diameter of the eye pupil are known in the art and mentioned, e.g., in U.S. Pat. No. 5,422,690. In FIG. 6, point X1-X2 corresponds to line X1-X2 in FIG. 5a, and point X3-X4 corresponds to line X3-X4 in FIG. 5a. The abnormality is revealed as nystagmus N4 during which the object is not seen by the patient.

Thus, it has been shown that the invention provides a universal method and apparatus for testing individuals with regard to abnormalities in spatial perception with the use of two screens installed in the close-vision field and the far-vision field by observing the patterns of the eye pupil movements in tracking the objects stationary or moving in the close screen, far screen, in both screens, and in switching from one screen to another. The invention also provides a method and apparatus that can detect abnormalities in spatial perception undetectable by other known methods and apparatuses, can be used for determining professional fitness of an individual to a specific profession, especially for professions associated with high risks, and can be used for testing the individuals with regard to spatial perception on the basis of personalized data bases accumulated for specific activities and for specified individuals.

Although the invention has been shown and described with reference to specific embodiments, it is understood that these embodiments should not be construed as limiting the areas of application of the invention and that any changes and modifications are possible, provided that these changes and modifications do not depart from the scope of the attached patent claims. For examples, the image sensor may be different from the given as an example. More than one abnormality of spatial perceptions may be detected in one person. The screens may have different profiles. In addition to horizontal linear and close-loop trajectories, the light spot can be moved in a vertical, diagonal or angular direction. An 8-shaped pattern can be used as a trajectory of the light spot on the screens. The image generator is not necessary a laser-based device and may comprise, e.g., an LCD screen.

The invention claimed is:

1. An apparatus for detecting abnormalities in spatial perception of a person to be tested comprising:
   a first transparent screen located at a first distance from the eyes of said person when the head of said person is in a stationary state;
   a second screen selected from a transparent screen and an opaque screen located at a second distance from the eyes of said person when the head of said person is in a stationary state, said second distance being greater than said first distance;
   means for forming a first image visible to said person on said first screen;
   means for forming a second image visible to said person on said second screen through said first screen;
   tracking means for tracking movements of at least one eye pupil of said person when said person follows images reproduced on said first screen and said second screen with his/her head being in a stationary state; and
   means for detecting abnormalities in spatial perception upon analyzing the tracking movements of the at least one pupil.

2. The apparatus of claim 1, wherein at least one of said first image and said second image is moveable.

3. The apparatus of claim 1, further provided with means for fixing the head of said person during testing.

4. The apparatus of claim 2, further provided with means for fixing the head of said person during testing.

5. The apparatus of claim 1, further provided with a central processing unit connected to said tracking means, said means for forming a first image and said means for forming said second image.

6. The apparatus of claim 2, further provided with a central processing unit connected to said tracking means, said means for forming a first image and said means for forming said second image.

7. The apparatus of claim 3, further provided with a central processing unit connected to said tracking means, said means for forming a first image and said means for forming said second image.

8. The apparatus of claim 1, wherein said first screen has a substantially flat shape, and wherein said second screen has a curvilinear shape with a concave side facing said person.

9. The apparatus of claim 7, wherein said first screen has a substantially flat shape, and wherein said second screen has a curvilinear shape with a concave side facing said person.

10. The apparatus of claim 7, wherein said first screen is located at a distance of 1 cm to 60 cm from said person's eyes and said second screen is located at a distance from said first screen to infinity from said person's eyes.

11. The apparatus of claim 5, wherein said central processing unit contains a data base with information that can be used as a reference.

12. The apparatus of claim 1, wherein said means for forming said first image and said means for forming said second image comprise means for forming moveable images.

13. The apparatus of claim 10, wherein said means for forming said first image and said means for forming said second image comprise means for forming moveable images.

14. A method of detecting abnormalities in spatial perception of a person to be tested comprising:
   providing a first transparent screen located at a first distance, a second screen located at a second distance that is greater than said first distance, and means for selectively producing images visible to said person on said first screen and on said second screen through said first screen, said person having different spatial perception of images at said first distance and said second distance;
   fixing the head of said person in a stationary state;
   producing an image tracked by said person on one of said first screen and said second screen while tracking the trajectory of movement of at least one eye pupil of said person;
   producing an image tracked by said person on the other of said first screen and said second screen while tracking the trajectory of movement of said at least one eye pupil of said person; and
   detecting abnormalities in spatial perception of said person for images on said first screen and on said second screen by manipulating with said images on said first screen and said second screen and detecting irregularities in said trajectories selected from the group comprising nystagmuses, cut-offs, sudden drop of the glance, curvilinear trajectory of the eye pupil when tracking linearly movements of said image on any of said first screen and said second screen, discontinuity of vision at the peripheral parts of said trajectories, and irregular changes in the eye pupil dimensions.

15. The method of claim 14, wherein said steps of producing an image on said first screen and said second screen comprise producing moving images selectively on said first screen and second screen along a trajectory selected from reciprocal linear movements between two points, reciprocal curvilinear movements between two points, and closed-loop movements.

16. The method of claim 14, wherein said step of detecting abnormalities is carried out with instantaneous switching of said images between said first screen and said second screen without changing the position of the head of said person.

17. The method of claim 14, wherein said first screen is located at a distance of 1 cm to 60 cm from said person's eyes and said second screen is located at a distance from said first screen to infinity from said person's eyes.

18. The method of claim 16, wherein said first screen is located at a distance of 1 cm to 60 cm from said person's eyes and said second screen is located at a distance from said first screen to infinity from said person's eyes.

19. The method of claim 15, wherein said moving images are moving light spots.

20. The method of claim 18, said moving images are moving light spots.

* * * * *